US00PP34757P2

(12) United States Plant Patent
Beekenkamp

(10) Patent No.: US PP34,757 P2
(45) Date of Patent: Nov. 22, 2022

(54) ***CELOSIA* PLANT NAMED 'BKCELLUMAG'**

(50) Latin Name: ***Celosia argentea* var. *cristata***
Varietal Denomination: BKCELLUMAG

(71) Applicant: BEEKENKAMP PLANTS B.V., Maasdijk (NL)

(72) Inventor: Annie Cornelia Beekenkamp, Maasdijk (NL)

(73) Assignee: BEEKENKAMP PLANTS B.V., Maasdijk (NL)

( * ) Notice: Subject to any disclaimer, the term of this patent is extended or adjusted under 35 U.S.C. 154(b) by 0 days.

(21) Appl. No.: 17/709,897

(22) Filed: Mar. 31, 2022

(51) Int. Cl.
*A01H 5/02* (2018.01)
*A01H 6/02* (2018.01)

(52) U.S. Cl.
USPC ..... Plt./263.1
CPC ..... *A01H 6/02* (2018.05)

(58) Field of Classification Search
USPC ..... Plt./263.1
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of *Celosia* plant named 'BKCELLUMAG', characterized by its broadly upright plant habit; moderately vigorous to vigorous growth habit; freely branching habit; freely flowering habit; magenta-colored flowers arranged on cristate-type inflorescences; and good interiorscape and garden performance.

2 Drawing Sheets

Figure 1:
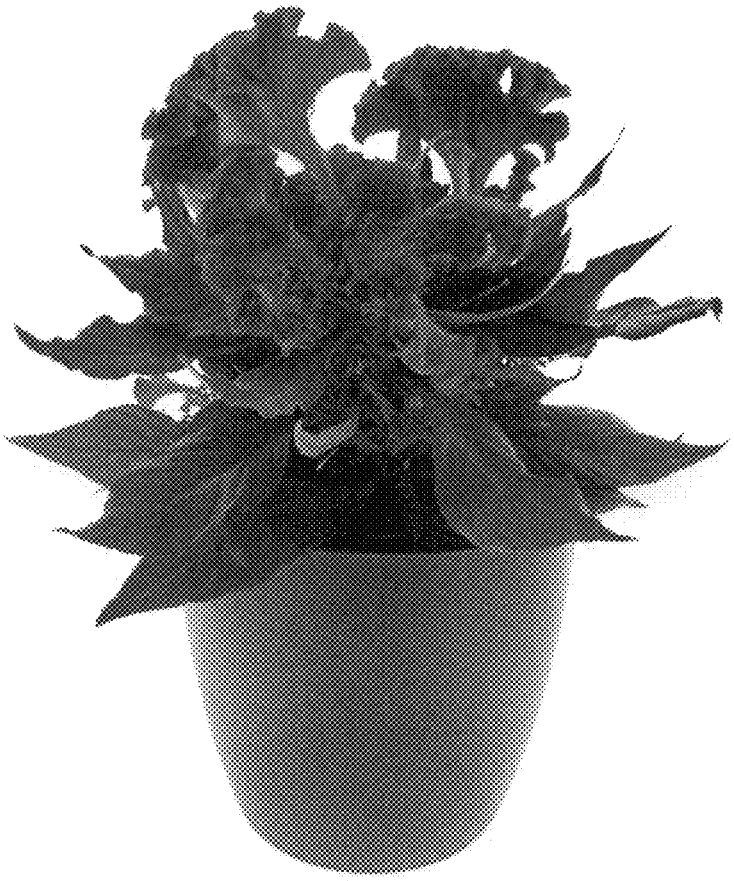

Botanical designation: *Celosia argentea* var. *cristata*.
Cultivar denomination: 'BKCELLUMAG'.

STATEMENT REGARDING PRIOR DISCLOSURES BY THE INVENTOR/APPLICANT & ASSIGNEE

An European Community Plant Breeder's Rights application for the instant plant was filed by the Applicant/Assignee, Beekenkamp Plants B.V. of Maasdijk, The Netherlands on Feb. 15, 2022, application number 2022/0477. Foreign priority is not claimed to this application.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct *Celosia* plant, botanically known as *Celosia argentea* var. *cristata*, commonly referred to as Cockscomb and hereinafter referred to by the name 'BKCELLUMAG'.

The new *Celosia* plant is a product of a planned breeding program conducted by the Inventor in Maasdijk, The Netherlands. The objective of the breeding program is to create new *Celosia* plants that have unique and attractive flowers, long flowering period and good interiorscape and garden performance.

The new *Celosia* plant originated from a self-pollination in Maasdijk, The Netherlands of a proprietary selection of

*Celosia argentea* var. *cristata* identified as code number 16-0011-01, not patented. The new *Celosia* plant was discovered and selected by the Inventor as a single flowering plant from within the progeny of the stated self-pollination in a controlled environment in Maasdijk, The Netherlands in April, 2017.

Asexual reproduction of the new *Celosia* plant by terminal vegetative cuttings in a controlled environment in Maasdijk, The Netherlands since April, 2018 has shown that the unique features of this new *Celosia* plant are stable and reproduced true to type in successive generations.

SUMMARY OF THE INVENTION

Plants of the new *Celosia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'BKCELLUMAG'. These characteristics in combination distinguish 'BKCELLUMAG' as a new and distinct *Celosia* plant:

1. Broadly upright plant habit.
2. Moderately vigorous to vigorous growth habit.
3. Freely branching habit.
4. Freely flowering habit.
5. Magenta-colored flowers arranged on cristate-type inflorescences.
6. Good interiorscape and garden performance.

Plants of the new *Celosia* differ from plants of the parent selection in the following characteristics:

1. Leaves of plants of the new *Celosia* are darker green than leaves of plants of the parent selection.

2. Flowers of plants of the new *Celosia* are magenta in color whereas flowers of plants of the parent selection are yellow in color.

Plants of the new *Celosia* can be compared to plants of *Celosia argentea* var. *cristata* 'Hot Topic Red', not patented. In side-by-side comparisons, plants of the new *Celosia* differ primarily from 'Hot Topic Red' in the following characteristics:

1. Plants of the new *Celosia* are taller than plants of 'Hot Topic Red'.
2. Leaves of plants of the new *Celosia* are darker green in color than leaves of plants of 'Hot Topic Red'.
3. Plants of the new *Celosia* have magenta-colored flowers whereas plants of 'Hot Topic Red' have red-colored flowers.

BRIEF DESCRIPTION OF THE PHOTOGRAPHS

The accompanying colored photographs illustrate the overall appearance of the new *Celosia* plant showing the colors as true as it is reasonably possible to obtain in colored reproductions of this type. Colors in the photographs may differ slightly from the color values cited in the detailed botanical description which accurately describe the colors of the new *Celosia* plant.

The photograph on the first sheet (FIG. 1) is a side perspective view of a typical flowering plant of 'BKCELLUMAG' grown in a container.

Figure 2:
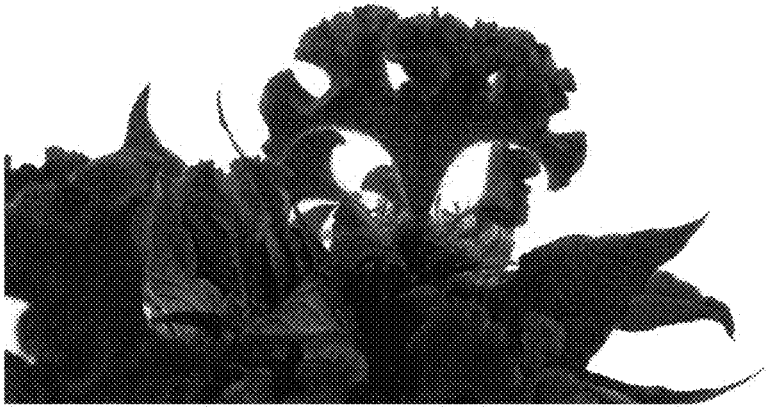

The photograph on the second sheet (FIG. 2) is a close-up view of typical inflorescences of 'BKCELLUMAG'.

DETAILED BOTANICAL DESCRIPTION

The aforementioned photographs and following observations, measurements and values describe plants grown in 12-cm containers during the winter in a glass-covered greenhouse in Maasdijk, The Netherlands and under commercial cultural practices typical of *Celosia* production. During the production of the plants, day temperatures ranged from 17° C. to 18° C. and night temperatures ranged from 15° C. to 16° C. Plants were pinched one time and were 14 weeks old when the photographs and description were taken. In the following description, color references are made to The Royal Horticultural Society Colour Chart, 2015 Edition, except where general terms of ordinary dictionary significance are used.

Botanical classification: *Celosia argentea* var. *cristata* 'BKCELLUMAG'.

Parentage:

*Female, or seed, parent*.—Proprietary selection of *Celosia argentea* var. *cristata* identified as code number 16-0011-01, not patented.

*Male, or pollen, parent*.—Proprietary selection of *Celosia argentea* var. *cristata* identified as code number 16-0011-01, not patented.

Propagation:

*Type*.—By terminal vegetative cuttings.

*Time to initiate roots, summer*.—About 16 days at temperatures ranging from about 19° C. to 21° C.

*Time to initiate roots, winter*.—About 19 days at temperatures ranging from about 19° C. to 21° C.

*Time to produce a rooted young plant, summer*.—About 21 days at temperatures ranging from about 19° C. to 21° C.

*Time to produce a rooted young plant, winter*.—About 23 days at temperatures ranging from about 19° C. to 21° C.

*Root description*.—Medium in thickness, fibrous; typically white in color, actual color of the roots is dependent on substrate composition, water quality, fertilizer type and formulation, substrate temperature and physiological age of roots.

*Rooting habit*.—Moderately freely branching; medium density.

Plant description:

*Plant form and growth habit*.—Herbaceous annual typically grown as a potted plant; upright plant habit; broadly ovate to nearly globular in overall shape; freely branching habit with about two basal branches each with about five lateral branches developing per plant; moderately vigorous to vigorous growth habit and moderate growth rate.

*Plant height, soil level to top of foliar plane*.—About 13.9 cm.

*Plant height, soil level to top of floral plane*.—About 16.1 cm.

*Plant width* (*spread*).—About 20.2 cm.

*Lateral branches*.—Length: About 6.2 cm. Diameter: About 4 mm. Internode length: About 4 mm. Strength: Moderately strong. Aspect: About 30° from vertical. Texture and luster: Moderately ribbed, glabrous; slightly glossy. Color, developing: Close to 186A to 186B. Color, developed: Close to 186B; at the internodes, close to a blend of 150C to 150D tinged with 186B.

Leaf description:

*Arrangement*.—Alternate; simple.

*Length*.—About 9.5 cm.

*Width*.—About 3.4 cm.

*Shape*.—Narrowly ovate to narrowly elliptic.

*Apex*.—Long apiculate.

*Base*.—Attenuate.

*Margin*.—Entire, moderately undulate.

*Texture and luster, upper surface*.—Smooth, glabrous; matte.

*Texture and luster, lower surface*.—Smooth, glabrous; slightly glossy.

*Venation pattern*.—Pinnate.

*Color*.—Developing leaves, upper surface: Close to 144A. Developing leaves, lower surface: Close to 144B. Fully expanded leaves, upper surface: Close to a blend of 137B and 138A; venation, close to 183A. Fully expanded leaves, lower surface: Close to 146B; venation, close to 177B.

*Petioles*.—Length: About 1.1 cm. Diameter: About 2.75 mm to 3 mm. Strength: Low, flexible. Texture and luster, upper and lower surfaces: Smooth, glabrous; slightly glossy. Color, upper surface: Close to 156A; towards the margins, close to 178B. Color, lower surface: Close to 159A; towards the margins, close to 182C.

Flower description:

*Flower type and arrangement*.—Single rotate flowers arranged in cristate-type terminal compound spikes; flowers face outwardly to slightly upward depending on position on spike.

*Flowering habit*.—Freely flowering habit with about 30 flowers per inflorescence and about 800 flowers developing per plant during the flowering season.

*Fragrance*.—None detected.

*Natural flowering season*.—Plants begin flowering about twelve weeks after pinching; under natural season conditions, flowering continuous from spring into the autumn in The Netherlands.

*Postproduction longevity*.—Inflorescences of the new *Celosia* have good longevity and plants maintain good substance for about five weeks on the plant; flowers persistent.

*Inflorescence height*.—About 6.6 cm.

*Inflorescence diameter*.—About 6 cm.

*Flower diameter*.—About 7 mm by 7 mm.

*Flower height*.—About 7 mm.

*Flower buds*.—Length: About 3 mm. Diameter: About 1.5 mm. Shape: Narrowly ovate. Texture and luster: Smooth, glabrous; velvety; glossy. Color: Close to N75C, 76C and 76D.

*Petals*.—None observed.

*Sepals*.—Quantity and arrangement: Typically six to eight per flower arranged in two whorls. Length: About 5 mm. Width: About 1.2 mm. Shape: Lanceolate, slightly concave. Apex: Narrowly acute. Base: Cuneate. Margin: Entire, not undulate. Texture and luster, inner and outer surfaces: Smooth, glabrous; glossy. Color: When opening, upper and lower surfaces: Close to 76C to 76D to lighter than 76D; midvein, close to 72B. Fully opened, upper and lower surfaces: Close to 76C to 76D to lighter than 76D; midvein, close to 72B; color becoming closer to 72C and 72D and midvein, closer to 72C, with development.

*Peduncles*.—Length: About 2.2 mm. Diameter: About 3 mm. Angle: Upright to about 55° from vertical. Strength: Moderately strong. Texture and luster: Smooth, glabrous; matte. Color: Close to a blend of 64B and 186A.

*Pedicels*.—Length: About 1 mm. Diameter: About 1 mm. Angle: About 80° from peduncle axis. Strength: Moderately strong. Texture and luster: Smooth, glabrous; matte. Color: Close to 187A.

*Reproductive organs*.—Stamens: Quantity per flower: Five. Filament length: About 2 mm. Filament color: Close to 76C; towards the base, close to 76D. Anther size: About 0.3 mm by 1 mm. Anther shape: Narrowly oblong. Anther color: Close to 185C to 185D. Pollen amount: Scarce. Pollen color: Close to 161C. Pistils: Quantity per flower: One. Length: About 3 mm. Stigma diameter: About 1 mm. Stigma shape: Club-shaped, three-parted. Stigma color: Close to 60A. Style length: About 2.75 mm. Style color: Close to 60A. Ovary color: Close to 185A to 185B.

*Floral bracts*.—Quantity and arrangement: One at the base of each pedicel. Length: About 5 mm. Diameter: About 0.75 mm. Shape: Narrowly lanceolate. Apex: Narrowly acuminate. Base: Cuneate. Color, upper and lower surfaces: Close to 75A.

*Crest*.—Height: About 4.7 cm. Width: About 2.5 cm to 6 cm. Color: Close to 183C to 183D; densely pubescent, hairs are close to 72B in color and towards the apex, more intense than a blend of 53A and 60A.

*Seeds and fruits*.—To date, seed and fruit development have not been observed on plants of the new *Celosia*.

Pathogen & pest resistance: To date, plants of the new *Celosia* have not been observed to be resistant to pathogens and pests common to *Celosia* plants.

Garden performance: Plants of the new *Celosia* have been observed to have good garden performance and to be suitable for USDA Hardiness Zones 9 to 12.

It is claimed:

1. A new and distinct *Celosia* plant named 'BKCELLUMAG' as illustrated and described.

* * * * *